United States Patent [19]

Pearson et al.

[11] 4,046,046
[45] Sept. 6, 1977

[54] MEAT CORING DEVICE INCLUDING A TEMPLATE

[75] Inventors: Gerald L. Pearson, Spencer, Iowa; Harold J. Tuma, Brookings, S. Dak.

[73] Assignee: Spencer Foods, Inc., Spencer, Iowa

[21] Appl. No.: 712,810

[22] Filed: Aug. 9, 1976

[51] Int. Cl.² .............................................. B26F 1/32
[52] U.S. Cl. ...................................... 83/745; 83/821; 83/919
[58] Field of Search .......................... 83/745, 821, 919; 30/174; 73/425, 425.2

[56] References Cited

U.S. PATENT DOCUMENTS

| 2,463,455 | 3/1949 | Dann | 83/919 X |
| 2,913,760 | 11/1959 | Engle, Jr. | 83/821 X |

Primary Examiner—Frank T. Yost

[57] ABSTRACT

A template device adapted to take a core of meat from a carefully controlled portion of a meat carcass including a template adapted to control the location and direction of the coring, and a coring tool adapted to be guided by the template to cut the core from the carcass.

3 Claims, 4 Drawing Figures

U.S. Patent  Sept. 6, 1977  Sheet 1 of 2  4,046,046

U.S. Patent  Sept. 6, 1977  Sheet 2 of 2  4,046,046

MEAT CORING DEVICE INCLUDING A TEMPLATE

BACKGROUND AND SUMMARY OF THE INVENTION

One of the principal concerns of the purchaser of beef, and particularly those who purchase the higher grades of beef is the matter of tenderness as well as good taste. Both qualities are difficult of objective measurement.

Up until the present, the customary way of ascertaining tenderness was by a visual examination of the carcass to see how much fat was dispersed through the muscle — principally the longissimus muscle from which the higher quality steaks were cut. However, this method is not accurate, and while not being completely invalid, is still of doubtful accuracy.

By our new method, and use of our new apparatus, we provide an objective and highly accurate measurement of the tenderness of the beef in any carcass.

FIGURES

Figure 1:
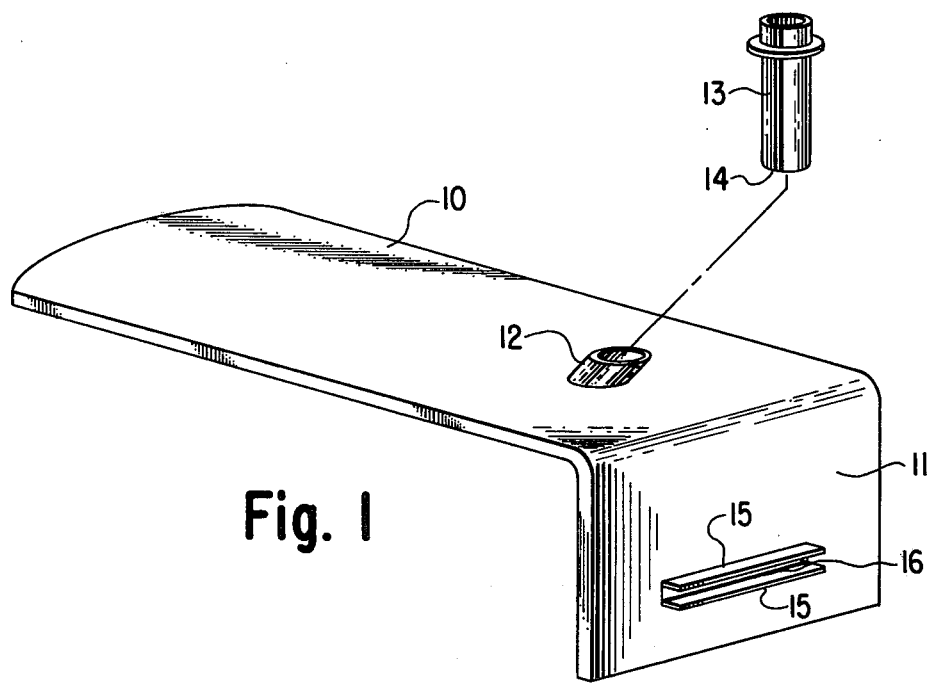
Figure 2:
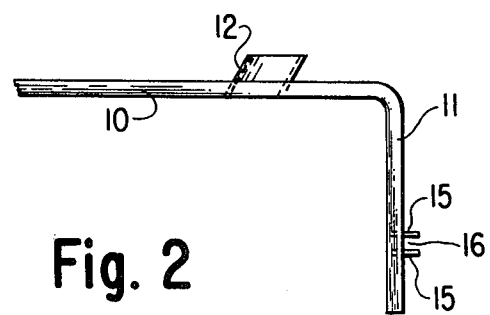
Figure 3:
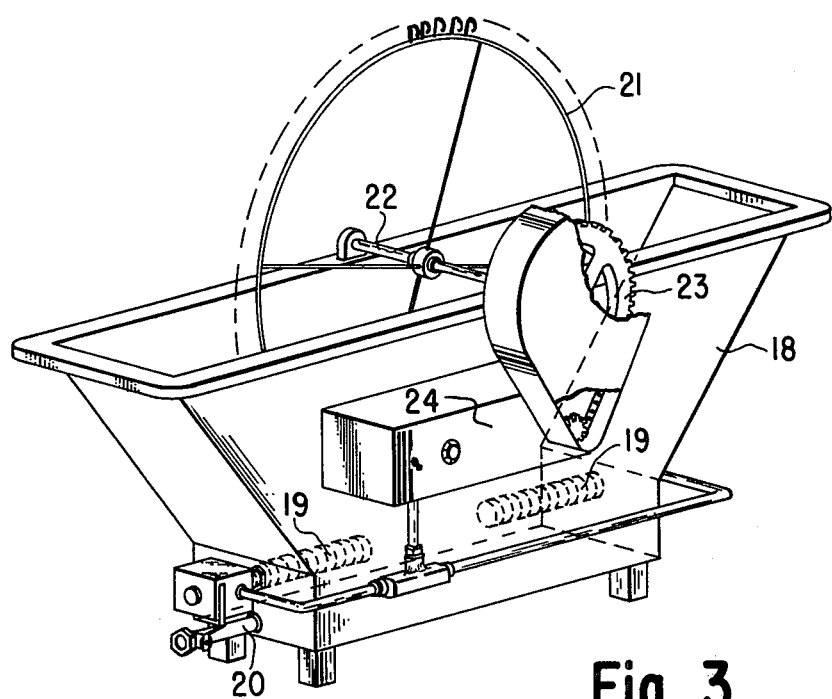
Figure 4:
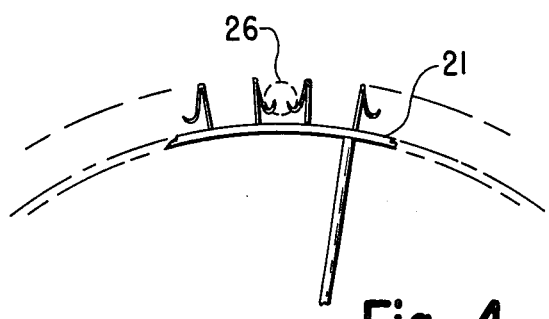

FIG. 1 is a pictorial view of the core gauging template and removing tool of my invention, FIG. 2 is a side elevational view of the template alone, FIG. 3 is a pictorial view of the cooking device used in our system, and FIG. 4 is a detailed view to an enlarged scale of the core holders on the cooking device.

DESCRIPTION

Briefly, our invention comprises a method of testing the tenderness of beef in a carcass by removing a core of the meat from a controlled part of the carcass, cooking the core and then measuring the force required to shear the core. It also includes the template and coring means for taking the core from the carcass, and the device for cooking the core.

More specifically, and referring to the drawings, we provide a template consisting of a piece of stainless steel having a longer leg 10 adapted to lie flat on the carcass and a shorter leg 11 substantially perpendicular to the longer leg. The shorter leg is adapted to be placed flat against the cut edge of the carcass at the 12th rib which is the location now used by examiners in evaluating the carcass. A tubular guide 12 is mounted on the longer leg 10. The opening through center of the guide tube is extended by forming a hole through that leg so that there is a continuous hole through the template.

A coring tool 13 having a sharpened lower edge 14 is slidably movable through the guide 12. In this way, the location and angular position of the coring tool is strictly controlled relative to the cut edge of the beef quarter. The angular position is important because the core must be taken parallel to the muscle fiber alignment. Normally this will be a 65° angle.

On the shorter leg 11, we provide a knife guide consisting of a pair of rails 15 spaced apart about the thickness of a knife blade and bracketing a slot 16 in the shorter leg. Thus, a knife can be uniformly guided into the meat to cut the lower end of the core loose from the surrounding meat and allow it to be withdrawn.

The method of determining the tenderness of the core depends on taking of the core uniformly from all carcasses, and by use of the template, this uniformity can be accomplished. After removal of the core from the carcass, it is placed in a bath of melted fat at a controlled temperature for a controlled time. We have found that a temperature of 250° F. for 2¾ minutes gives the best results. The goal is to provide a uniform and medium degree of doneness without abnormal protein coagulation or surface crustiness which would interfere with the shearing.

A device for cooking the cores is illustrated in FIGS. 3 and 4. In this device, a vat or container 18 is provided to hold the heated fat. Heating coils 19 at each end of the container serve to provide a controlled amount of heat to hold the fat at a pre-set temperature. Thermostatic controls 20 are provided to be sensitive to the temperature and to control the amount of heat provided.

A wheel 21 is rotatably mounted so that it will turn into and out of the fat. Thus, it can carry a series of cores of meat through the heated fat in the container 18. The wheel is mounted on an axle 22, which in turn is driven by a chain drive 23 from a motor mounted in a housing 24 on the container. The motor should be one capable of being controlled to a substantially constant speed, and will probably need to be geared down to provide proper speed to turn the wheel through the fat at a speed in which the core will be properly cooked in one pass.

Each core 26 is held at the periphery of the wheel 20 by pointed fingers on which the core can be impaled and from which it can easily be removed. It will be seen that by providing a fixed temperature of the fat and a fixed speed of the wheel — and therefore a fixed time during which the core is cooked in the fat — we can provide a closely controlled set of parameters in which the variable is the character or quality of meat in the core.

After cooking, the core is sheared by a device, well known in the art as a Warner-Bratzler shearing device. By using this device, we can determine the force required to shear the cooked core and hence the tenderness of the core. We prefer to shear the core twice to provide an average reading so that some unusual circumstance in a part of core does not provide a false reading.

We have discovered by several tests that there is a very high correlation between our shear tenderness results and the opinion of human taste panel evaluation of tenderness — much higher than the correlation between expert graders and the opinion of similar taste panels. Therefore, we are convinced that by controlling the location on the carcass from which the core is removed and the conditions under which it is prepared and sheared, we have provided a valid, objective method of testing the tenderness of a beef carcass.

We claim:

1. A tool for removing a core from a carcass comprising template means having two legs perpendicular to each other, one of said legs being formed to provide a hole therethrough, core cutting means slidably disposed in said hole and being guided by the walls thereof at a controlled angle, and knife guiding means on the other of said legs through which a knife blade may be inserted to cut off the core at a controlled position.

2. The device of claim 1 in which tubular guide means extends from said first named leg, the inner opening of said guide means being continuous with the walls of said hole in said leg.

3. The device of claim 1 in which said knife guiding means comprises a slot formed in said second named leg and rail means on said second named leg are immediately adjacent said slot.

* * * * *